US010950364B2

(12) United States Patent
Hatakeyama et al.

(10) Patent No.: US 10,950,364 B2
(45) Date of Patent: *Mar. 16, 2021

(54) BIO-ELECTRODE AND METHOD FOR MANUFACTURING THE SAME

(71) Applicant: SHIN-ETSU CHEMICAL CO., LTD., Tokyo (JP)

(72) Inventors: Jun Hatakeyama, Jyoetsu (JP); Motoaki Iwabuchi, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 1010 days.

This patent is subject to a terminal disclaimer.

(21) Appl. No.: 15/484,514

(22) Filed: Apr. 11, 2017

(65) Prior Publication Data

US 2017/0323698 A1    Nov. 9, 2017

(30) Foreign Application Priority Data

May 9, 2016    (JP) .............................. JP2016-93996

(51) Int. Cl.
*H01B 1/22*    (2006.01)
*A61B 5/0408*    (2006.01)
(Continued)

(52) U.S. Cl.
CPC .............. *H01B 1/22* (2013.01); *A61B 5/0245* (2013.01); *A61B 5/0402* (2013.01);
(Continued)

(58) Field of Classification Search
CPC ..... A61B 5/04; A61B 5/0408; A61B 5/04886; A61B 5/6813; A61B 5/683
See application file for complete search history.

(56) References Cited

U.S. PATENT DOCUMENTS 5,981,680 A    11/1999    Petroff et al.
6,951,559 B1    10/2005    Greep
(Continued)

FOREIGN PATENT DOCUMENTS

JP    H11-209714 A    8/1999
JP    2002-332305 A    11/2002
(Continued)

OTHER PUBLICATIONS

Nov. 5, 2018 Office Action Issued in Korean Patent Application No. 2017-0056747.
(Continued)

*Primary Examiner* — Eun Hwa Kim
*Assistant Examiner* — Christine A Dedoulis
(74) *Attorney, Agent, or Firm* — Oliff PLC

(57) ABSTRACT

The present invention provides a bio-electrode including an electro-conductive base material and a living body contact layer formed on the electro-conductive base material; wherein the living body contact layer contains a resin layer and particles dispersed in the resin layer, the particles being coated with gold, platinum, silver, or alloy of these metals; a thickness of the resin layer is equal to or thinner than an average particle size of the particles; the resin layer contains a silicon-containing resin and a non-silicon-containing resin; and the silicon-containing resin is localized in the direction of a surface of the resin layer. The bio-electrode of the present invention is superior in electric conductivity and biocompatibility, light in weight, can be manufactured at low cost, and can combine repellency of the resin layer surface and adhesion properties of the resin layer to particles.

11 Claims, 3 Drawing Sheets

(51) Int. Cl.
*A61B 5/0402* (2006.01)
*A61B 5/0245* (2006.01)
*A61B 5/00* (2006.01)
*H01B 3/44* (2006.01)

(52) U.S. Cl.
CPC ........ *A61B 5/04087* (2013.01); *A61B 5/6804* (2013.01); *A61B 2562/125* (2013.01); *H01B 3/441* (2013.01); *H01B 3/447* (2013.01)

(56) References Cited

U.S. PATENT DOCUMENTS

| | | | |
|---|---|---|---|
| 7,718,212 B2* | 5/2010 | Nesbitt | ............... B65G 49/064 427/2.1 |
| 2002/0188069 A1 | 12/2002 | Sugo et al. | |
| 2005/0107713 A1 | 5/2005 | Van Herk et al. | |

FOREIGN PATENT DOCUMENTS

| | | |
|---|---|---|
| JP | 2004-033468 A | 2/2004 |
| JP | 2005-320418 A | 11/2005 |
| JP | 2006-156068 A | 6/2006 |
| JP | 2011-079946 A | 4/2011 |
| JP | 2011-204530 A | 10/2011 |
| JP | 2012205884 A * | 10/2012 |
| JP | 2015-100673 A | 6/2015 |
| JP | 2015-109268 A | 6/2015 |
| KR | 2004-0095336 A | 11/2004 |
| WO | 2013/039151 A1 | 3/2013 |

OTHER PUBLICATIONS

May 31, 2019 Korean Office Action issued in Korean Patent Application No. 10-2017-0056747.

* cited by examiner (A)

(B)

(C)

(D)

BIO-ELECTRODE AND METHOD FOR MANUFACTURING THE SAME

TECHNICAL FIELD

The present invention relates to a bio-electrode, which is in contact with living skin and can detect physical conditions such as a heart rate on the basis of electric signals from the skin, and a method for manufacturing the same.

BACKGROUND ART

In recent years, wearable devices have been developed progressively with the spread of Internet of Things (IoT). Representative examples thereof include a watch and glasses that can be connected with internet. Wearable devices that can always monitor physical conditions are also necessary in a medical field and a sports field, and is expected to be a growth field in the future.

In the medical field, wearable devices have been investigated to monitor organic conditions by sensing a weak current such as an electrocardiogram measurement, which detects heart beats by electric signals. The electrocardiogram is measured by fitting a body with electrodes on which electro-conductive paste is applied, and this measurement is performed only once in a short period of time. On the other hand, the aim of development of the foregoing medical wearable device is to develop devices that monitor health conditions continuously for several weeks. Accordingly, bio-electrodes used for a medical wearable device have to keep the electric conductivity unchanged and not to cause skin allergies even when being used for a long time. In addition to these, it is desirable that the bio-electrode is light in weight and can be manufactured at low cost.

Medical wearable devices include a type in which the device is attached to a body and a type in which the device is incorporated into clothes. As the type in which the device is attached to a body, it has been proposed a bio-electrode using water soluble gel containing water and electrolyte, which are materials of the foregoing electro-conductive paste (Patent Document 1). On the other hand, as the type in which the device is incorporated into clothes, it has been proposed a means to use cloth in which a conductive polymer such as poly-3,4-ethylenedioxythiophene-polystyrenesulfonate (PEDOT-PSS) or silver paste is incorporated into the fibers for electrodes (Patent Document 2).

When using the foregoing water soluble gel containing water and electrolyte, however, the electric conductivity is lost as the water is lost due to drying. The use of metal with high ionization tendency such as copper has a risk to cause skin allergies to some people. The use of an electro-conductive polymer such as PEDOT-PSS also has a risk of skin allergies due to the strong acidity of the electro-conductive polymer.

As the electrode material, it has been investigated to use metal nanowire, carbon black, and carbon nanotube since they have excellent electric conductivity. The metal nanowire can conduct electricity in a small loading amount since the wires are brought into contact with each other in high probability. The metal nanowire, however, can cause skin allergies since they are thin material with sharp tips. The carbon nanotube cannot be used too, by the same reason. The carbon black is irritative to skin, although the toxicity is lower than the carbon nanotube. As described above, the biocompatibility is sometimes worsened due to the shape and irritation of a material, even though the material itself does not cause an allergic reaction. Accordingly, it has been difficult to combine the electric conductivity and the biocompatibility.

As a means for solving these problems, it has been investigated to use electro-conductive metal particles as an electrode material. Among metals, noble metals such as gold, platinum, and silver, which have lowest ionization tendencies, are hard to cause skin allergies. Accordingly, it is possible to achieve both the electric conductivity and the biocompatibility by using these noble metal particles. When mixing these noble metal particles into a resin, however, electricity is not conducted unless the particles are brought into contact with each other in the resin, which is an insulator. In order to bring the particles into contact with each other, the noble metal particles have to be loaded in a volume ratio of 70% or more. As described above, when using metal particles, it is necessary to load a large amount of expensive noble metal particles, and accordingly, the production cost becomes very high and the weight increases, thereby making it impossible to achieve weight reduction, which is necessary for wearable devices.

It is said that skins show elongation of about 170%. Wearable devices attached to a body have to possess such properties of high elongation and high strength that they can follow the elongation of skins. Urethanes with low crosslink density show high elongation and high strength. Accordingly, stretchable urethanes having acryl based adhesive mass (tackiness agent) are widely used as a wound tape. The urethane base tapes having acryl based adhesive mass, however, makes skins red when they are adhered for a long time. The urethane also has a disadvantage of failing to repel perspiration due to the high hydrophilic nature (i.e., low repellency), which causes lowering of the elongation and strength due to hydrolysis. Meanwhile, silicones have high repellency and hardly irritate skins, and have been increasingly used as a skin adhesive mass thereby. Silicones, however, are inferior to urethane and so on in mechanical strength and in adhesion properties to noble metal particles as a resin to be mixed therewith.

PRIOR ART DOCUMENTS

Patent Documents

Patent Document 1: International Patent Laid-Open Publication No. WO 2013/039151
Patent Document 2: Japanese Unexamined Patent publication (Kokai) No. 2015-100673

SUMMARY OF INVENTION

Technical Problem

The present invention has been accomplished to solve the foregoing problems, and an object thereof is to provide a bio-electrode that is superior in electric conductivity and biocompatibility, light in weight, can be manufactured at low cost, and can combine repellency of the resin layer surface and adhesion properties of the resin layer to particles; as well as a method for manufacturing the same.

Solution to Problem

To achieve the object, the present invention provides a bio-electrode comprising an electro-conductive base material and a living body contact layer formed on the electro-conductive base material;

wherein the living body contact layer comprises a resin layer and particles dispersed in the resin layer, the particles being coated with gold, platinum, silver, or alloy of these metals; a thickness of the resin layer is equal to or thinner than an average particle size of the particles; the resin layer contains a silicon-containing resin and a non-silicon-containing resin; and the silicon-containing resin is localized in the direction of a surface of the resin layer.

Such a bio-electrode can be a bio-electrode that is superior in electric conductivity and biocompatibility, light in weight, can be manufactured at low cost, and can combine repellency of the resin layer surface and adhesion properties of the resin layer to particles.

It is preferable that the average particle size of the particles be 1 μm or more and 1,000 μm or less, and the thickness of the resin layer be 0.5 μm or more and 1,000 μm or less.

When the particles have such an average particle size, and the resin layer has such a thickness, the bio-electrode can be lighter while ensuring its sufficient electric conductivity, and the production cost can be reduced.

It is preferable that the ratio of the thickness of the resin layer to the average particle size of the particles be 0.5 or more and 1.0 or less.

Such a ratio of the thickness of the resin layer to the average particle size of the particles enables the resin layer to hold the particles sufficiently, and to effectively prevent lowering of the electric conductivity due to separation of particles.

It is preferable that the particles constitute 0.5% or more and 50% or less in a volume ratio on the basis of a total volume of the resin layer and the particles.

Such a volume ratio of the particles enables the bio-electrode to be lighter while ensuring its sufficient electric conductivity, and to reduce the production cost.

The resin layer is preferably a cured product of a resin composition comprising the silicon-containing resin and the non-silicon-containing resin, and each of the silicon-containing resin and the non-silicon-containing resin is at least one of a thermosetting resin and a photo-curable resin.

Such a resin layer can be formed easily, and is suitable for the inventive bio-electrode thereby.

It is also preferable that the silicon-containing resin contain one or more moieties selected from an ester bond, an amide bond, an imide bond, a urethane bond, a thiourethane bond, and a urea bond, together with a (meth)acrylate group; and the non-silicon-containing resin contains one or more moieties selected from an ester bond, an amide bond, an imide bond, a urethane bond, a thiourethane bond, and a thiol group, together with a (meth)acrylate group.

Such a silicon-containing resin can make the resin layer surface have excellent repellency, and can make the resin layer hardly lower the elongation and strength since the resin is hardly hydrolyzed. That is, it is possible to make the bio-electrode be less susceptive to perspiration. Such a silicon-containing resin is less irritative to skins, which can further improve the biocompatibility. In addition, when the non-silicon-containing resin is such a resin, the resin layer comes to have more favorable mechanical strength and adhesion properties to an electro-conductive base material and particles.

The electro-conductive base material preferably comprises one or more species selected from gold, silver, silver chloride, platinum, aluminum, magnesium, tin, tungsten, iron, copper, nickel, stainless, chromium, titanium, and carbon.

Such an electro-conductive base material can be suitably used for the inventive bio-electrode.

The particles are preferably spherical particles.

Such particles can conduct electricity from a living body more uniformly, and can further reduce irritation to skin in fitting.

The particles are preferably resin particles or inorganic particles coated with gold, platinum, silver, or alloy of these metals; the resin particles comprising one or more resins selected from polyacrylate, polyethylene, polypropylene, polystyrene, silicone, and polyurethane; and the inorganic particles comprising any of glass, silica, and quartz.

Such particles are lighter and lower in cost compared to particles entirely composed of gold, platinum, silver, or alloy of these metals. Accordingly, it is possible to make the bio-electrode lighter, and to reduce the production cost.

It is preferable that the particles each have an electro-conductive metal layer comprising one or more electro-conductive metals selected from silver, aluminum, copper, nickel, tungsten, and tin in an interior of the particle.

Such particles can give electric conductivity by the electro-conductive metal layer in the particle even when the gold, platinum, silver, or alloy of these metals on the surface of the particles are thinned, thereby making it possible to further reduce the production cost while ensuring sufficient electric conductivity.

It is also preferable that the thickness of the resin layer be thinner than the average particle size of the particles, and the particles be exposed convexly from the surface of the resin layer.

When the particles are exposed convexly from the surface of the resin layer as described above, the contact area between the particles and a living body increases, and accordingly, it is possible to efficiently pick a weak current from a living body.

The particles are preferably disposed such that each of the particles is the only particle in a thickness direction of the resin layer.

Such arrangement of particles makes it possible to reduce the required amount of particles to a minimum while ensuring sufficient electric conductivity. Accordingly, the bio-electrode can be lighter, and the production cost can be reduced.

The present invention also provides a method for manufacturing a bio-electrode comprising: applying a composition comprising particles, a silicon-containing resin, a non-silicon-containing resin, and organic solvent, the particles being coated with gold, platinum, silver, or alloy of these metals and dispersed in the composition, onto an electro-conductive base material; baking the composition to evaporate the organic solvent while localizing the silicon-containing resin in the direction of a surface; and curing the silicon-containing resin and the non-silicon-containing resin under pressure to form a resin layer comprising the silicon-containing resin localized in the direction of the surface; thereby forming a living body contact layer comprising the particles and the resin layer having a thickness equal to or thinner than an average particle size of the particles on the electro-conductive base material.

Such a manufacturing method can manufacture a bio-electrode that is superior in electric conductivity and biocompatibility, light in weight, and combines repellency of the resin layer surface and adhesion properties of the resin layer to particles at low cost.

It is preferable that the organic solvent have a boiling point in a range of 115 to 200° C. at atmospheric pressure.

Such organic solvents can be evaporated at a temperature where the silicon-containing resin and the non-silicon-containing resin do not cure, and is favorable for the inventive method for manufacturing a bio-electrode.

The organic solvent, having a boiling point in a range of 115 to 200° C. at atmospheric pressure, is preferably one or more solvent selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, and propylene glycol monoethyl ether acetate.

These solvents each have a boiling point in the range described above, thereby being particularly favorable for the inventive method for manufacturing a bio-electrode.

It is preferable that the average particle size of the particles be 1 µm or more and 1,000 µm or less, and the resin layer be formed to have a thickness of 0.5 µm or more and 1,000 µm or less.

By using the particles having such an average particle size, and making the resin layer have such a thickness, it is possible to manufacture a bio-electrode having a lighter weight while ensuring its sufficient electric conductivity, and to reduce the production cost.

It is preferable that the resin layer be formed to have a thickness with a ratio of the thickness to the average particle size of the particles being 0.5 or more and 1.0 or less.

Such a ratio of the thickness of the resin layer to the average particle size of the particles enables the resin layer to hold the particles sufficiently. Accordingly, it is possible to manufacture a bio-electrode in which lowering of the electric conductivity due to separation of particles is effectively prevented.

It is preferable that the particles constitute 0.5% or more and 50% or less in a volume ratio on the basis of a total volume of the formed resin layer and the particles.

Such a volume ratio of the particles makes it possible to manufacture a bio-electrode having a lighter weight while ensuring its sufficient conductivity, and to reduce the production cost.

It is preferable that the silicon-containing resin and the non-silicon-containing resin be each at least one of a thermosetting resin and a photo-curable resin, and are cured by either or both of heat and light.

Such resins can be cured by such methods to form the resin layer easily.

It is preferable that the silicon-containing resin contain one or more moieties selected from an ester bond, an amide bond, an imide bond, a urethane bond, and a urea bond, together with a (meth)acrylate group; and the non-silicon-containing resin contain one or more moieties selected from an ester bond, an amide bond, an imide bond, a urethane bond, a thiourethane bond, and a thiol group, together with a (meth)acrylate group.

The use of such a silicon-containing resin can make the resin layer surface have excellent repellency, and can make the resin layer hardly lower the elongation and strength since the resin is hardly hydrolyzed. That is, it is possible to manufacture a bio-electrode less susceptive to perspiration. Such a silicon-containing resin is less irritative to skins, which can further improve the biocompatibility. In addition, the use of such a non-silicon-containing resin makes it possible to manufacture a bio-electrode in which the resin layer has more favorable mechanical strength and adhesion properties to an electro-conductive base material and particles.

It is preferable that the electro-conductive base material comprise one or more species selected from gold, silver, silver chloride, platinum, aluminum, magnesium, tin, tungsten, iron, copper, nickel, stainless, chromium, titanium, and carbon.

Such an electro-conductive base material can be suitably used for the inventive method for manufacturing a bio-electrode.

It is preferable that the particles be spherical particles.

By using such particles, it is possible to manufacture a bio-electrode that can conduct electricity from a living body more uniformly, and can further reduce irritation to skin in fitting.

It is preferable that the particles be resin particles or inorganic particles coated with gold, platinum, silver, or alloy of these metals; the resin particles comprising one or more resins selected from polyacrylate, polyethylene, polypropylene, polystyrene, silicone, and polyurethane; and the inorganic particles comprising any of glass, silica, and quartz.

Such particles are lighter and lower in cost compared to particles entirely composed of gold, platinum, silver, or alloy of these metals. Accordingly, by using these particles, it is possible to produce a bio-electrode having a lighter weight, and to reduce the production cost.

It is preferable that the particles each have an electro-conductive metal layer comprising one or more electro-conductive metals selected from silver, aluminum, copper, nickel, tungsten, and tin in an interior of the particle.

Such particles can give electric conductivity by the electro-conductive metal layer in the particle even when the gold, platinum, silver, or alloy of these metals on the surface of the particles are thinned. Accordingly, by using these particles, it is possible to further reduce the production cost while ensuring sufficient electric conductivity.

It is preferable that the resin layer be formed to have a thickness thinner than the average particle size of the particles, and the particles be exposed convexly from the surface of the resin layer.

When the particles are exposed convexly from the surface of the resin layer as described above, it is possible to increase the contact area between the particles and a living body, and to improve the efficiency to pick a weak current from a living body.

It is preferable that the particles be disposed such that each of the particles is the only particle in a thickness direction of the resin layer.

Such arrangement of particles makes it possible to suppress the required amount of particles to a minimum while ensuring sufficient electric conductivity. Accordingly, it is possible to manufacture a bio-electrode having a lighter weight, and to reduce the production cost.

Advantageous Effects of Invention

As described above, the inventive bio-electrode can efficiently conduct electric signals from skin to a device (i.e., having excellent electric conductivity), is free from the risk of causing allergies even when it is worn on skin for a long time (i.e., having excellent biocompatibility), can reduce the required amount of particles to a minimum, which makes the bio-electrode be lighter, and can be manufactured at low cost. In the inventive bio-electrode, the resin layer contains a silicon-containing resin and a non-silicon-containing resin, and the silicon-containing resin with excellent repellency is localized in the direction of the surface of the resin layer, which can bring excellent repellency on the resin layer surface. The inventive bio-electrode also contains a non-silicon-containing resin, not only the silicon-containing resin, which can make the resin layer have more favorable mechanical strength and adhesion properties to an electro-conductive base material and particles. That is, the inventive bio-electrode can combine repellency of the resin layer surface and adhesion properties of the resin layer to particles. By adjusting the composition and the thickness of the resin layer appropriately, it is possible to prevent lowering of the electric conductivity due to wetting by perspiration from a living body, drying, or separation of the particles; and to improve elasticity and tackiness to a living body. Accordingly, such an inventive bio-electrode is particularly suitable for a bio-electrode used for a medical wearable device. Moreover, the inventive method for manufacturing a bio-electrode can manufacture such a bio-electrode easily at low cost.

DESCRIPTION OF EMBODIMENTS

As described above, when a bio-electrode uses particles made of noble metal such as gold and platinum, the biocompatibility becomes excellent. In order to obtain sufficient electric conductivity, however, it is necessary to load a large amount of noble metal particles so as to bring the particles in contact with each other. The use of a large amount of expensive noble metal materials increases the production cost, and the containing of a large amount of particles causes an increase of the weight. When the resin layer is formed by using either a non-silicon-containing resin such as urethane or a silicon-containing resin such as silicone alone, it is impossible to combine repellency of the resin layer surface and adhesion properties of the resin layer to particles.

The present inventors have diligently investigated to solve the foregoing subject. As a result, the inventors have found that by using particles coated with gold, platinum, silver, or alloy of these metals, which is hard to cause skin allergies, as the electro-conductive particles loaded into the living body contact layer, and making the thickness of the resin layer equal to or thinner than the average particle size of the particles, it is possible to achieve both the electric conductivity and the biocompatibility, and to suppress the required amount of particle, which can bring lighter weight and reduction of the production cost. The inventors have also found that by making the resin layer contain both of a silicon-containing resin having excellent repellency and a non-silicon-containing resin having excellent adhesion properties to particles, and by localizing the silicon-containing resin in the direction of the surface of the resin layer (on the side to be in contact with a body), it is possible to combine repellency of the resin layer surface and adhesion properties of the resin layer to particles; thereby completing the present invention.

That is, the present invention is a bio-electrode comprising an electro-conductive base material and a living body contact layer formed on the electro-conductive base material;

wherein the living body contact layer comprises a resin layer and particles dispersed in the resin layer, the particles being coated with gold, platinum, silver, or alloy of these metals; a thickness of the resin layer is equal to or thinner than an average particle size of the particles; the resin layer contains a silicon-containing resin and a non-silicon-containing resin; and the silicon-containing resin is localized in the direction of a surface of the resin layer.

Hereinafter, the inventive bio-electrode will be specifically described with reference to the Figures, but the present invention is not limited thereto.

<Bio-Electrode>

Figure 1:
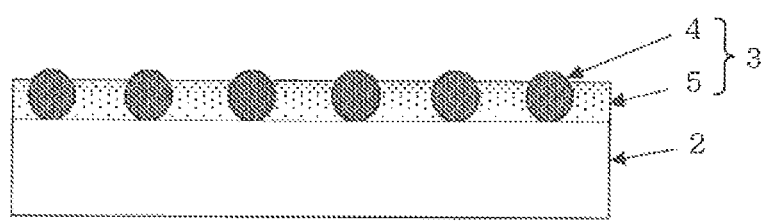
FIG. 1 is a schematic sectional view showing an example of the inventive bio-electrode.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 comprises the resin layer 5 and the particles 4, the surface of which are coated with gold, platinum, silver, or alloy of these metals, dispersed in the resin layer 5. The thickness of the resin layer 5 is equal to or thinner than the average particle size of the particles 4. That is, a side of the surface of each particle 4 comes out on the surface of the side that is in contact with a living body (i.e., the particles 4 are exposed convexly from the surface of the resin layer 5, in other words, the particles 4 protrude in convex shapes from the surface of the resin layer 5), and the opposite side of the surface of each particle 4 is in contact with the electro-conductive base material 2. Moreover, the particles 4 are disposed such that each of the particles 4 is the only particle in a thickness direction of the resin layer 5, without stacking with each other. The resin layer 5 contains both of a silicon-containing resin and a non-silicon-containing resin, and the silicon-containing resin is localized in the direction of a surface of the resin layer 5. It is to be noted that FIG. 1 schematically shows the distribution of the silicon-containing resin by using a shade of color of the resin layer 5, and the silicon-containing resin is localized in the direction of a surface of the resin layer, which has a deeper shade.

Figure 2:
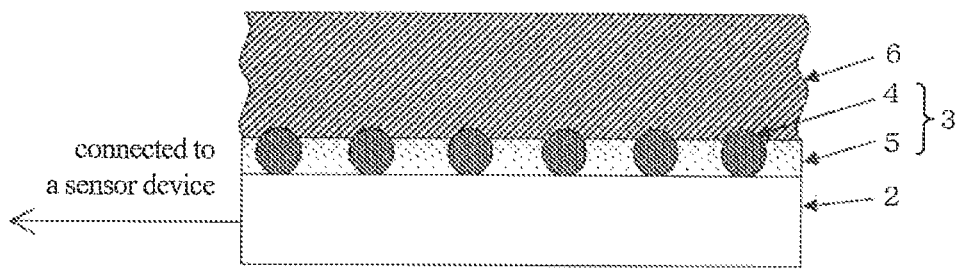
FIG. 2 is a schematic sectional view showing an example of the inventive bio-electrode worn on a living body.

When using the bio-electrode 1 of FIG. 1, electric signals are picked from a living body 6 through particles 4 while bringing the living body contact layer 3 (i.e., particles 4 and the resin layer 5) to be in contact with the living body 6, and then conducted to a sensor device (not shown) through the electro-conductive base material 2, as shown in FIG. 2. In the inventive bio-electrode, the thickness of the resin layer is equal to or thinner than the average particle size of the particles, and accordingly, the amount of particles required for conducting can be suppressed to a minimum. Moreover, since the particles are exposed convexly from the surface of the resin layer, the contact area between the particles and a living body is large, which brings excellent electric conductivity.

Figure 6:
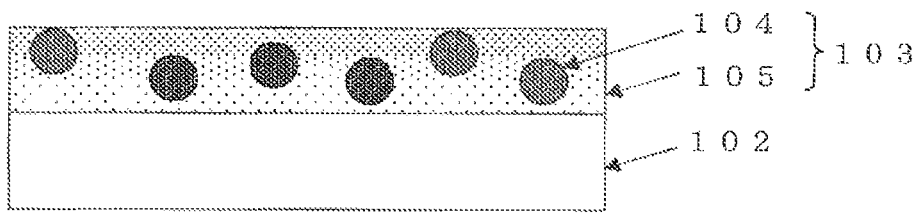
FIG. 6 is a schematic sectional view showing the bio-electrode of Comparative Example 3, in which the thickness of the resin layer was thicker than the average particle size of the particles since pressing was not performed in the curing.

Herein, FIG. 6 shows an example of a bio-electrode in which the thickness of the resin layer is thicker than the average particle size of the particles. In the bio-electrode 121 of FIG. 6, the living body contact layer 103 comprising the particles 104 and the resin layer 105 is formed on the electro-conductive base material 102, the resin layer 105 contains both of a silicon-containing resin and a non-silicon-containing resin, and the silicon-containing resin is localized in the direction of the surface of the resin layer 105. The resin layer 105, however, has a thickness thicker than the average particle size of the particles 104. That is, the particles 104 are not in contact with the electro-conductive base material 102, and are not exposed on the surface of the side that is in contact with a living body. Moreover, the particles 104 are not in contact with each other. Accordingly, electricity from a living body does not conducted to the electro-conductive base material 102.

Hereinafter, each component composing the inventive bio-electrode will be specifically described.

[Electro-Conductive Base Material]

The inventive bio-electrode comprises an electro-conductive base material. This electro-conductive base material is usually connected electrically with a sensor device and so on, and conducts electrical signals picked from a living body through the particles to the sensor device, etc.

The electro-conductive base material is not particularly limited as long as it is electro-conductive. However, it is preferable to comprise one or more species selected from gold, silver, silver chloride, platinum, aluminum, magnesium, tin, tungsten, iron, copper, nickel, stainless, chromium, titanium, and carbon, for example.

The electro-conductive base material is not particularly limited, and may be appropriately selected based on the use of the bio-electrode. Illustrative examples thereof include a hard electro-conductive substrate and an electro-conductive film having flexibility, which may be flat, uneven, or a meshed shape in which metal wires are woven. In order to increase the contact area with spherical particles, the electro-conductive base material preferably has unevenness, rather than a flat shape.

[Living Body Contact Layer]

The inventive bio-electrode comprises a living body contact layer formed on the electro-conductive base material. This living body contact layer is a part to be in contact with a living body actually when using the bio-electrode. This living body contact layer comprises a resin layer and particles dispersed in the resin layer, the surfaces of the particles being coated with gold, platinum, silver, or alloy of these metals.

(Particles)

In the inventive bio-electrode, the particles composing the living body contact layer are electro-conductive particles, each surface of which is coated with gold, platinum, silver, or alloy of these metals, and is intended to pick weak electrical signals from a living body and to conduct this to the foregoing electro-conductive base material.

The particles are preferably resin particles or inorganic particles coated with gold, platinum, silver, or alloy of these metals; the resin particles comprising one or more resins selected from polyacrylate, polyethylene, polypropylene, polystyrene, silicone, and polyurethane; and the inorganic particles comprising any of glass, silica, and quartz. Such particles are lighter and lower in cost compared to particles entirely composed of gold, platinum, silver, or alloy of these metals. Accordingly, it is possible to make the bio-electrode lighter, and to reduce the production cost.

The outmost surface of the particle, being in contact with skin, have to be gold, platinum, silver, or alloy of these metals, which is a noble metal without causing skin allergies. In the interior of the particle, however, an electro-conductive metal layer comprising one or more electro-conductive metals selected from silver, aluminum, copper, nickel, tungsten, tin, etc. may be contained. It is effective to make the outmost surface layer as thin as possible for reducing the cost since gold and platinum are expensive. If the layer of gold, platinum, etc. is too thin, however, the electric conductivity is lowered. Accordingly, it is effective to ensure the necessary electric conductivity by forming an electro-conductive metal layer comprising metal selected from silver, aluminum, copper, nickel, tungsten, and tin, etc., which are low cost, in the interior of the particle. Incidentally, the thickness of the gold, platinum, silver, or alloy of these metals on the particle surface is not particularly limited. However, it is preferably set to about several nm since the production cost can be reduced by thinning this layer as described above.

The average particle size of the particles, the surface of which being coated with gold, platinum, silver, or alloy of these metals, is preferably 1 μm or more and 1,000 μm or less, more preferably 2 μm or more and 800 μm or less, and further preferably 3 μm or more and 600 μm or less. When the average particle size of the particles is 1 μm or more, it is not difficult to form the resin layer, which have to be formed with the thickness being equal to or thinner than an average particle size of the particles. When the average particle size of the particles is 1,000 μm or less, there is no risk of difficulty for holding the particles, which is caused by too large particles, or excessive increase of the weight of the bio-electrode.

Incidentally, it is preferable that the variation of the particle size be as small as possible. More specifically, the standard deviation of the particle size when measuring 10 pieces of the particles is preferably 10% or less on the basis of the average particle size, and is more preferably, 5% or less on the basis of the average particle size. As the variation of the particle size is smaller, the exposure ratio of the particles exposed from the surface of the resin layer (i.e., the contact area between the particles and a living body) becomes more uniform, and the electric conductivity from a living body becomes more uniform thereby.

The particles are preferably spherical particles. The spherical particles makes it possible to conduct electricity from a living body more uniformly. It is also possible to reduce the irritation to skin in wearing the bio-electrode. Although the shape of the particle is most preferably a spherical shape, but can be an ellipse, a quadrilateral, a cone, and the other indeterminate forms.

As the spherical particle in which the surface of a resin particle is coated with gold, platinum, silver, or alloy of these metals, it is also possible to use the ones previously used as an electro-conductive adhesive and a spacer for conducting Liquid Crystal Display (LCD) and its driving circuit. Illustrative examples of such a particle include the ones described in Japanese Unexamined Patent publication (Kokai) No. H11-209714, Japanese Unexamined Patent publication (Kokai) No. 2006-156068, Japanese Unexamined Patent publication (Kokai) No. 2011-204530, and Japanese Unexamined Patent publication (Kokai) No. 2015-109268.

(Resin Layer)

In the inventive bio-electrode, the foregoing particles are dispersed in the resin layer composing the living body contact layer. The resin layer is a layer to prevent separation of these particles from the living body contact layer, and to hold the particles. In the present invention, the resin layer contains both of a silicon-containing resin and a non-silicon-containing resin, and the silicon-containing resin is localized in the direction of a surface of the resin layer.

Such a resin layer has good adhesion properties to the electro-conductive base material and the particles as well as high water repellency and slight tendency to be hydrolyzed, which can make the bio-electrode be less susceptible to perspiration. That is, it is possible to achieve both water repellency and adhesion properties.

The resin layer is preferably a cured product of a resin composition comprising the silicon-containing resin and the non-silicon-containing resin, and each of the silicon-containing resin and the non-silicon-containing resin is at least one of a thermosetting resin and a photo-curable resin.

Curing improves the adhesion properties of the resin layer to both of the particles and the electro-conductive base material. The curing means is not particularly limited, and general means can be used. For example, it is possible to use crosslinking reaction by either or both of heat and light, an acid catalyst, or a base catalyst. The crosslinking reaction can be performed by appropriately selecting a crosslinking agent described in "Kakyou han-nou handbook (handbook of crosslinking reaction)", Yasuharu Nakamura, Maruzen shuppan (2013), for example.

As will be described below, in manufacturing the inventive bio-electrode, an electro-conductive base material is coated with a composition comprising particles, a silicon-containing resin, a non-silicon-containing resin, and organic solvent. This is subjected to baking to evaporate the organic solvent while localizing the silicon-containing resin in the direction of a surface, and then subjected to contact bonding and stretching with a mold, for example. Accordingly, the silicon-containing resin and the non-silicon-containing resin preferably have low viscosity before curing. It is also preferable to select materials with low vapor pressure as the silicon-containing resin, the non-silicon-containing resin, and a crosslinking agent that will be described below in view of stability of curing.

In the inventive bio-electrode, the resin layer preferably has a good adhesion properties to the foregoing particles coated with gold, platinum, silver, or alloy of these metals in order to prevent lowering of the conductivity due to separation of particles from the resin layer. In the inventive bio-electrode, the resin layer preferably has a good adhesion properties to the electro-conductive base material in order to prevent peeling off of the living body contact layer from the electro-conductive base material. To enhance the adhesion properties of the resin layer to the electro-conductive base material and the particles coated with gold, platinum, silver, or alloy of these metals, it is effective to use highly polar resins as the silicon-containing resin and the non-silicon-containing resin (particularly, the non-silicon-containing resin). Illustrative examples of such a resin includes a resin that contains one or more moieties selected from an ester bond, an amide bond, an imide bond, a urethane bond, a thiourethane bond, and a thiol group; as well as a polyacrylic resin, polyamide resin, polyimide resin, polyurethane resin, and polythiourethane resin. In the inventive bio-electrode, it is preferable to use a resin having a structure described above as the silicon-containing resin and the non-silicon-containing resin to form the resin layer. Hereinafter, the silicon-containing resin and the non-silicon-containing resin will be more specifically described.

—Silicon-Containing Resin—

In the resin layer of the inventive bio-electrode, the silicon-containing resin is a component that localizes in the direction of a surface of the resin layer to enhance the repellency of the resin layer surface, and making the resin layer be hardly hydrolyzed. The silicon-containing resin may be a silicone resin, and may be polyacrylic resin, polyamide resin, polyimide resin, polyurethane resin, and polythiourethane resin, each of which contains a silicon atom, for example.

The silicon atom-containing polyacrylic resin includes a polymer that has a silicone main chain and a polymer that has a silicon atom(s) on the side chain. Each of them can be suitably used. As the polymer that has a silicone main chain, silsesquioxane or siloxane having a (meth)acrylpropyl group and so on can be used. In this case, an addition of a photoradical generator allows the (meth)acryl moiety to polymerize to cure.

When the side chain of the silicone contains a double bond(s) such as a vinyl group and an allyl group, photo-crosslinking can be performed by adding a thiol type crosslinking agent. It is to be noted that the thiol coordinates to gold. Accordingly, when using particles coated with gold, an addition of thiol gives an effect to improve the adhesiveness between the particles and the resin layer. In this case, the silicone does not necessarily have an ester bond, an amide bond, an imide bond, a urethane bond, and a thiourethane bond.

Illustrative examples of the suitable silicon atom-containing polyamide resin include polyamide silicone resins described in Japanese Unexamined Patent publication (Kokai) No. 2011-079946 and U.S. Pat. No. 5,981,680, for example. Such a polyamide silicone resin can be synthesized by combining a silicone or non-silicone compound having amino groups at the both terminals and a non-silicone or silicone compound having carboxy groups at the both terminals. When the silicone has a (meth)acrylpropyl group(s) at the side chain, it can be cured by photoradical crosslinking. When the silicone has a vinyl group(s) and an SiH group(s) (silicon atom-containing hydrogen atom), it can be crosslinked through an addition reaction by a platinum catalyst.

It is also possible to use polyamic acid before cyclization thereof, which is obtained by reacting carboxylic anhydride and amine. The carboxy group of the polyamic acid may be crosslinked by using a crosslinking agent such as an epoxy type and an oxetane type. It is also possible to esterify the carboxy group with hydroxyethyl (meth)acrylate, and to perform photoradical crosslinking of the (meth)acrylate moiety.

Illustrative examples of the suitable silicon atom-containing polyimide resin include polyimide silicone resins described in Japanese Unexamined Patent publication (Kokai) No. 2002-332305, for example. Although polyimide resins have very high viscosity, it can be changed to have low viscosity by blending a (meth)acrylic monomer as a solvent and a crosslinking agent.

Illustrative examples of the silicon atom-containing polyurethane resin include polyurethane silicone resins. These polyurethane silicone resins can be crosslinked through urethane bond by blending a compound having isocyanate groups at the both terminals and a compound having hydroxy groups at the terminal, and heating the same. In this case, a silicon atom(s) (siloxane bond) have to be contained in either or both of the compound having isocyanate groups at the both terminals and the compound having hydroxy groups at the terminal. Alternatively, a urethane (meth) acrylate monomer and polysiloxane can be blended and photo-crosslinked as described in Japanese Unexamined Patent publication (Kokai) No. 2005-320418. It is also possible to perform photo-crosslinking of a polymer having both of a siloxane bond(s) and a urethane bond(s), with the terminal having a (meth)acrylate group(s).

The silicon atom-containing polythiourethane resin can be obtained by reacting a compound having a thiol group(s) and a compound having an isocyanate group(s), and either of them have to contain a silicon atom(s). Photo-curing is also possible if (meth)acrylate groups are contained at the terminals.

Among these silicon-containing resins, particularly preferable silicon-containing resin contains one or more moieties selected from an ester bond, an amide bond, an imide bond, a urethane bond, a thiourethane bond, and a urea bond, together with a (meth)acrylate group.

Such a silicon-containing resin makes the resin layer have good repellency on the surface, and be hardly hydrolyzed, thereby hardly lowering the elongation and strength. That is, it is possible for a bio-electrode to be less susceptible to perspiration. These silicon-containing resins are less irritative to skins, which makes the biocompatibility more favorable.

—Non-Silicon-Containing Resin—

In the resin layer of the inventive bio-electrode, the non-silicon-containing resin is a component to improve the adhesion properties of the resin layer to particles and the electro-conductive base material, and to make the resin layer have excellent mechanical strength.

The non-silicon-containing resin preferably contains one or more moieties selected from an ester bond, an amide bond, an imide bond, a urethane bond, a thiourethane bond, and a thiol group, together with a (meth)acrylate group.

Illustrative examples of such resins include polyester-(meth)acrylate, polyamide-(meth)acrylate, polyimide-(meth)acrylate, polyurethane-(meth)acrylate, polythiourethane-(meth)acrylate, polythiol-(meth)acrylate, and copolymers thereof. Among them, polyurethane-(meth) acrylate is particularly preferable.

Such a non-silicon-containing resin makes the resin layer have particularly favorable mechanical strength and adhesion properties to the electro-conductive base material and particles.

To perform photo-crosslinking, it is preferable to use a resin having (meth)acrylate terminals or adding a crosslinking agent having a terminal(s) of (meth)acrylate or a thiol group(s), together with adding a photoradical generator, which generates a radical by light.

Illustrative examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoic acid, 2-(1,3-benzodioxole-5-yle)-4,6-bis(trichloroethyl)-1,3,5-triazine, 2-benzyl-2-(dimethylamino)-4'-morpholinobutylophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl) phosphine oxide, 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone (BAPO). The loading amount of the photoradical generator is preferably in a range of 0.1 to 50 parts by mass on the basis of 100 parts by mass of the resin.

To the composition for forming the resin layer, an adhesion improving agent may be added in order to improve the adhesion property of the resin layer and the particles. Illustrative examples of such an adhesion improving agent include silane coupling agents having a thiol group, a hydroxy group, a carboxy group, an amide group, and a urethane group.

Since the inventive bio-electrode is used by being attached to a living body (e.g., skin), the composition for forming the resin layer may contain a tackifier in order to add tackiness to a living body. Illustrative examples of such a tackifier include a silicone resin other than the foregoing silicon-containing resin and non-crosslinkable siloxane.

It is to be noted that the thickness of the resin layer is preferably 0.5 µm or more and 1,000 µm or less, more preferably 1 µm or more and 800 µm or less, further preferably 2 µm or more and 600 µm or less.

The thickness of the resin layer is preferably in the ratio to the average particle size of the particles being 0.5 or more and 1.0 or less. In such a ratio, the resin layer can hold the particles sufficiently, and can effectively prevent lowering of the electric conductivity due to separation of the particles thereby.

In the inventive bio-electrode, it is preferable that the thickness of the resin layer be thinner than the average particle size of the particles, and the particles be exposed convexly from the surface of the resin layer. When the particles are exposed convexly from the surface of the resin layer as described above, the contact area between the particles and a living body increases, and weak current from a living body can be efficiently picked thereby.

In the inventive bio-electrode, it is also preferable that the particles constitute 0.5% or more and 50% or less in a volume ratio on the basis of a total volume of the resin layer and the particles (i.e., the volume of the living body contact layer). Such a volume ratio of the particles allows the bio-electrode to be lighter in weight while ensuring sufficient electric conductivity, and to reduce the production cost.

In the inventive bio-electrode, the particles are preferably disposed such that each of the particles is the only particle in the thickness direction of the resin layer. Such an arrangement of the particles can suppress the required amount of particles to a minimum while ensuring sufficient electric conductivity, which can make the bio-electrode lighter, and can reduce the production cost.

In the inventive bio-electrode, it is also possible to separately provide a tacky film on the living body contact layer or in the surroundings in order to prevent peeling off of the bio-electrode from a living body during the use as in the previous bio-electrodes (e.g., the bio-electrode described in Japanese Unexamined Patent publication (Kokai) No. 2004-033468). The tacky film may be formed by using tackiness agent of an acrylic type, a urethane type, a silicone type, etc., when it is formed. Particularly, the silicone type is suitable since it has high oxygen permeability to allow the skin to breathe during wearing the bio-electrode, has high repellency to reduce lowering of tackiness due to perspiration, and is less irritative to skins. It is to be noted that the foregoing tacky film is not essential to the inventive bio-electrode since the silicon-containing resin is localized in the direction of a surface of the resin layer, and the peeling off from a living body can be prevented by adding the tackifier to the composition for forming the resin layer or using a resin having good tackiness to a living body as described above.

When the inventive bio-electrode is used as a wearable device, the components including the wiring between the bio-electrode and a sensor device are not particularly limited. For example, it is possible to apply the ones described in Japanese Unexamined Patent publication (Kokai) No. 2004-033468.

As described above, the inventive bio-electrode can efficiently conduct electric signals from skin to a device (i.e., having excellent electric conductivity), is free from the risk of causing allergies even when it is worn on skin for a long time (i.e., having excellent biocompatibility), can suppress the required amount of particles to a minimum, which makes the bio-electrode lighter, and can be manufactured at low cost. The inventive bio-electrode has a resin layer in which a silicon-containing resin and a non-silicon-containing resin are contained, and the silicon-containing resin with excellent repellency is localized in the direction of a surface of the resin layer; and can have excellent repellency of the resin layer surface thereby. The resin layer also contains a non-silicon-containing resin, not only a silicon-containing resin, whereby it is also possible to improve the mechanical strength and adhesion properties to the electro-conductive base material and particles. That is, the inventive bio-electrode can combine repellency of the resin layer surface and adhesion properties of the resin layer to particles. By adjusting the composition and the thickness of the resin layer appropriately, it is possible to prevent lowering of the electric conductivity due to wetting by perspiration from a living body, drying, or separation of the particles; and to improve elasticity and tackiness to a living body. Accordingly, such an inventive bio-electrode is particularly suitable for a bio-electrode used for a medical wearable device.

<Method for Manufacturing Bio-Electrode>

The present invention also provides a method for manufacturing a bio-electrode comprising: applying a composition comprising particles, a silicon-containing resin, a non-silicon-containing resin, and organic solvent, the particles being coated with gold, platinum, silver, or alloy of these metals and dispersed in the composition, onto an electro-conductive base material; baking the composition to evaporate the organic solvent while localizing the silicon-containing resin in the direction of a surface; and curing the silicon-containing resin and the non-silicon-containing resin under pressure to form a resin layer comprising the silicon-containing resin localized in the direction of the surface; thereby forming a living body contact layer comprising the particles and the resin layer having a thickness equal to or thinner than an average particle size of the particles on the electro-conductive base material.

Hereinafter, the inventive method for manufacturing a bio-electrode will be specifically described with reference to the Figures, but the inventive method for manufacturing a bio-electrode is not limited thereto.

Figure 3:
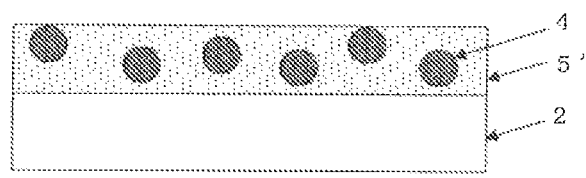
FIG. 3 is an explanatory drawing showing an example of the inventive method for manufacturing a bio-electrode.
Figure 3:
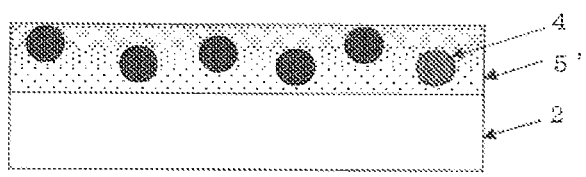
Figure 3:
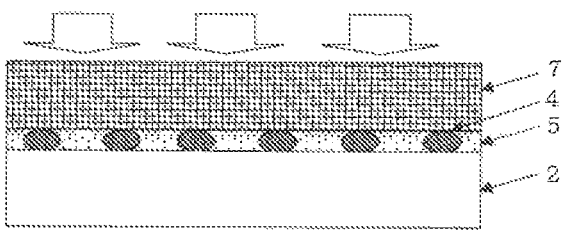
Figure 3:
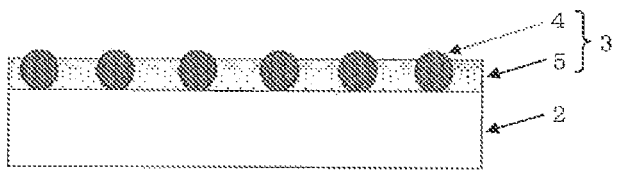

FIG. 3 is an explanatory drawing showing an example of the inventive method for manufacturing a bio-electrode. In the manufacturing method of FIG. 3, the electro-conductive base material 2 is initially coated with a composition (the resin layer material 5') comprising the particles 4 being coated with gold, platinum, silver, or alloy of these metals, a silicon-containing resin, a non-silicon-containing resin, and organic solvent, with the particles 4 being dispersed therein, as shown in FIG. 3(A). Then, as shown in FIG. 3(B), baking is performed to evaporate the organic solvent while localizing the silicon-containing resin in the direction of a surface. Subsequently, as shown in FIG. 3(C), the silicon-containing resin and the non-silicon-containing resin are crosslinked and cured while pressing with the mold 7 to form the resin layer 5, in which the silicon-containing resin is localized in the direction of the surface. In this case, although the particles 4 deform by pressing, the shapes of the particles 4 return to their original shapes by removing the mold 7 after curing, thereby making it possible to form the cured resin layer 5 to have a thickness equal to or thinner than the average particle size of the particles 4 as shown in FIG. 3(D). These procedures make it possible to manufacture a bio-electrode in which the living body contact layer 3 is formed on the conductive base material 2, with the living body contact layer 3 comprising the resin layer 5 and particles 4 dispersed in the resin layer 5, as shown in FIG. 3(D).

It is to be noted that in the inventive method for manufacturing a bio-electrode, it is possible to use the same ones described above as the conductive base material, the particles being coated with gold, platinum, silver, or alloy of these metals, the silicon-containing resin, the non-silicon-containing resin, the thickness of the resin layer and the volume ratio of the particles in the bio-electrode to be manufactured, etc.

It is preferable that the organic solvent used for the composition have a boiling point in a range of 115 to 200° C. at atmospheric pressure. Illustrative examples thereof include 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, and propylene glycol monoethyl ether acetate; and it is preferable to use one or more solvent selected therefrom.

Such organic solvents can be evaporated at a temperature where the silicon-containing resin and the non-silicon-containing resin do not cure, and is favorable for the inventive method for manufacturing a bio-electrode.

The method for applying the composition onto the electro-conductive base material is not particularly limited. It is suitable to use a method such as dip coating, spray coating, spin coating, roll coating, flow coating, and doctor coating.

The baking after applying the composition is preferably performed at a temperature that can evaporate the organic solvent in the composition without curing the silicon-containing resin and the non-silicon-containing resin. The baking temperature may be appropriately selected in accordance with types of the silicon-containing resin, the non-silicon-containing resin, and the organic solvent used for the composition. It is preferable to set the baking temperature about 115 to 200° C., for example.

The method for curing the resin is not particularly limited, and can be appropriately selected based on a kind of resin used for the resin layer. However, the resin is preferably cured by either or both of heat and light, for example. The foregoing composition can also be cured by adding a catalyst to generate acid or base, which causes a crosslinking reaction.

In case of heating, the temperature is not particularly limited, and may be appropriately selected based on a kind of resin used for the resin layer. However, it is preferable to be about 50 to 250° C. for example.

When curing is performed by photo-polymerization reaction (e.g., photo-crosslinking by radicals), the mold used for pressing is preferably a transparent material with high optical transmission (e.g., transparent substrate). Incidentally, in curing by light, heating is not essential.

When the heating and light irradiation are combined, it is possible to perform the heating and the light irradiation simultaneously, to perform the heating after the light irradiation, or to perform the light irradiation after the heating.

In curing, the resin have to be cured under pressure (press curing). The pressure in the press curing is not particularly limited, but is preferably 0.01 to 100 kg/cm², for example. It is possible to adjust the thickness of the resin layer and the heights of the convexly exposed particles based on the foregoing deform extent of the particles. The thickness of the resin layer can also be adjusted by the distance between the mold 7 and the electro-conductive base material 2 in the pressing. It is also possible to heat while pressing in order to improve the fluidity of the resin during pressing and to accelerate the crosslinking reaction.

As described above, the inventive method for manufacturing a bio-electrode can easily manufacture the inventive bio-electrode that is superior in electric conductivity and biocompatibility, is light in weight, and combines repellency of the resin layer surface and adhesion properties of the resin layer to the particles at low cost.

EXAMPLES

Hereinafter, the present invention will be specifically described with reference to Examples and Comparative Examples, but the present invention is not limited thereto. Incidentally, the weight average molecular weight (Mw) represents a weight average molecular weight in terms of polystyrene determined by gel permeation chromatography (GPC).

The particles coated with gold, platinum, silver, or alloy of these metals used in Examples and Comparative Examples are Micropearl AU (manufactured by SEKISUI CHEMICAL CO. LTD.) with the average particle size of 40 ("Au-40" in Table) and Micropearl AU with the average particle size of 100 μm ("Au-100" in Table), which are spherical particles coated with gold; and Ag-coat powders (manufactured by Mitsubishi Materials Electronic Chemicals Co., Ltd.), which are spherical particles coated with silver with the average particle size of 30 μm ("Ag-30" in Table).

The following are Silicone-(meth)acrylates-1 to 16 each blended to compositions for forming a living body contact layer as a silicon-containing resin.

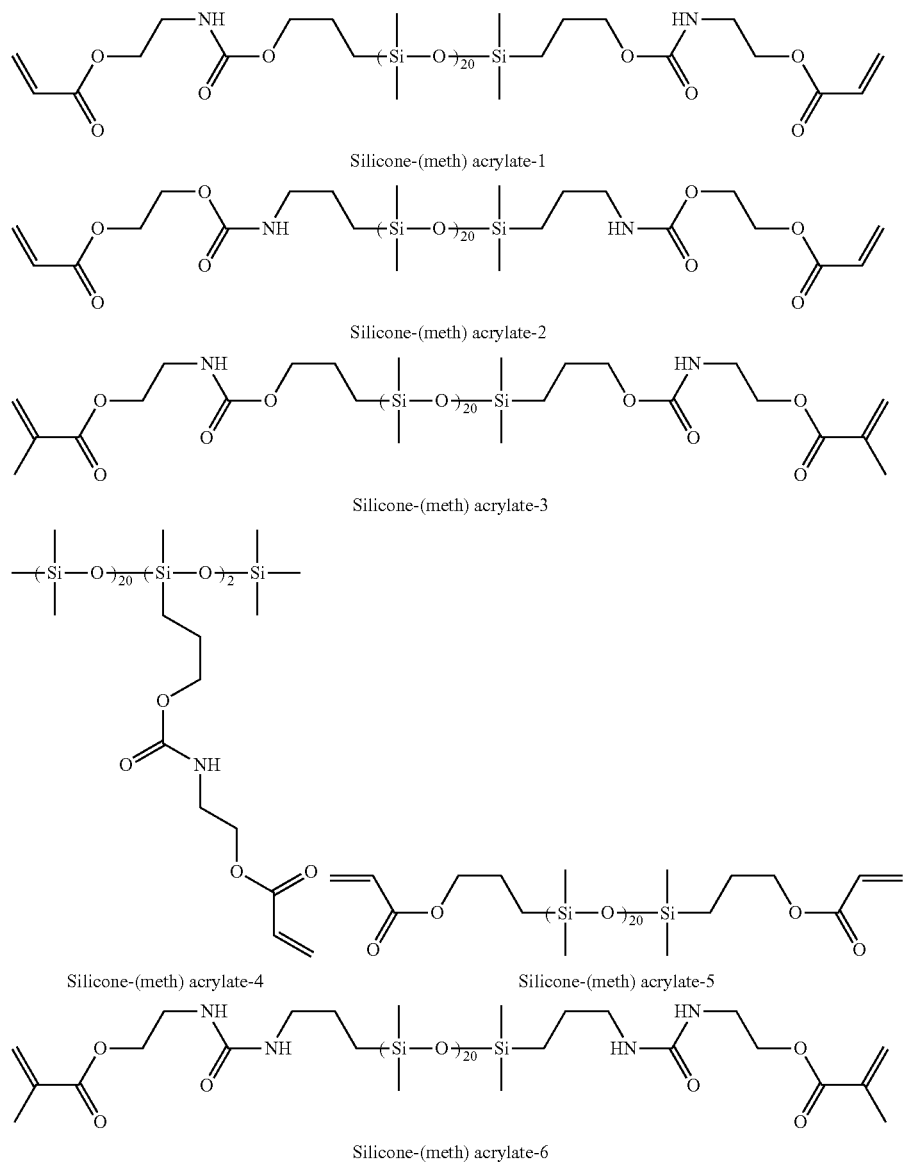

(In the formulae, the numbers of repeating units are average values)
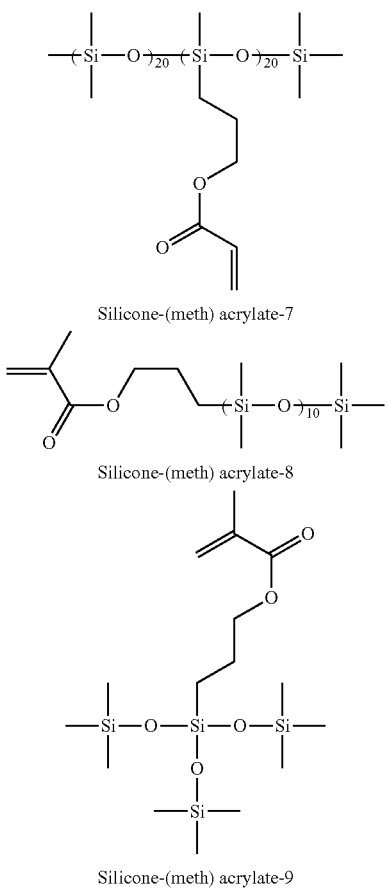
Silicone-(meth) acrylate-7
Silicone-(meth) acrylate-8
Silicone-(meth) acrylate-9
-continued
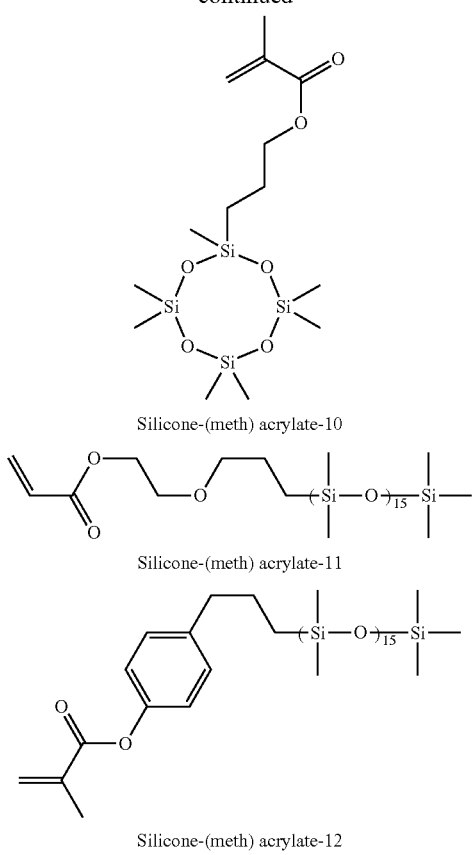
Silicone-(meth) acrylate-10
Silicone-(meth) acrylate-11
Silicone-(meth) acrylate-12
(In the formulae, the numbers of repeating units are average values)
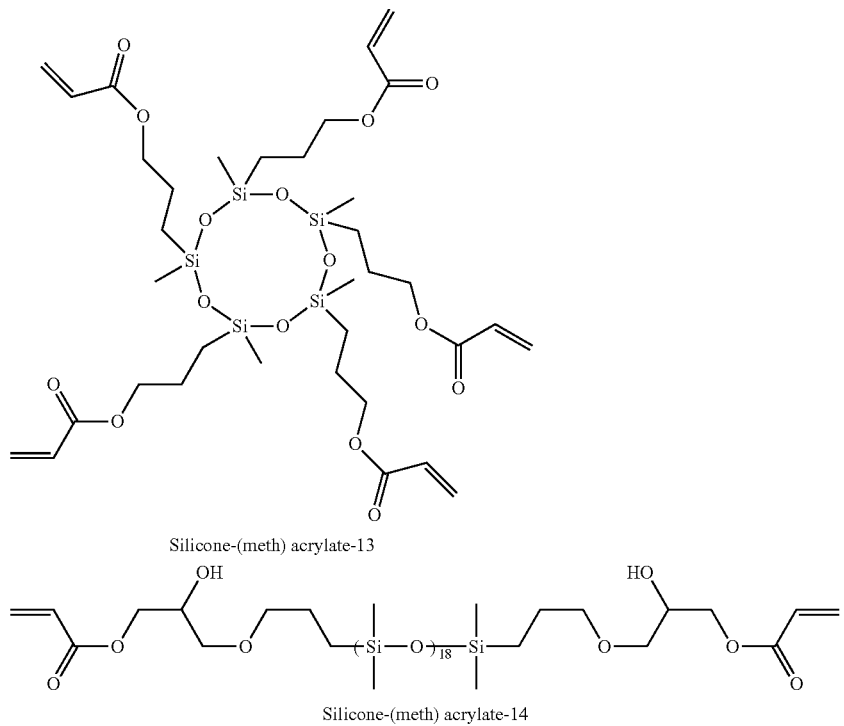
Silicone-(meth) acrylate-13
Silicone-(meth) acrylate-14

-continued

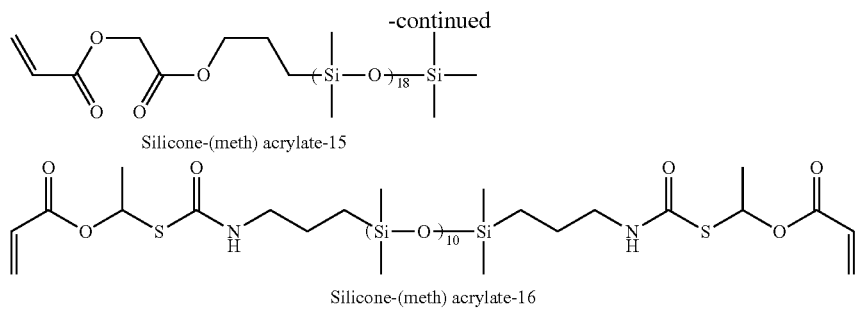

Silicone-(meth) acrylate-15

Silicone-(meth) acrylate-16

(In the formulae, the numbers of repeating units are average values)

Silicone-(meth)acrylate-1:
  Molecular weight (Mw)=1,940, Dispersity (Mw/Mn)=1.8
Silicone-(meth)acrylate-2:
  Molecular weight (Mw)=1,980, Dispersity (Mw/Mn)=1.6
Silicone-(meth)acrylate-3:
  Molecular weight (Mw)=1,970, Dispersity (Mw/Mn)=1.6
Silicone-(meth)acrylate-4:
  Molecular weight (Mw)=1,840, Dispersity (Mw/Mn)=1.9
Silicone-(meth)acrylate-5:
  Molecular weight (Mw)=1,760, Dispersity (Mw/Mn)=1.6
Silicone-(meth)acrylate-6:
  Molecular weight (Mw)=2,010, Dispersity (Mw/Mn)=1.5
Silicone-(meth)acrylate-7:
  Molecular weight (Mw)=1,950, Dispersity (Mw/Mn)=1.8
Silicone-(meth)acrylate-8:
  Molecular weight (Mw)=940, Dispersity (Mw/Mn)=1.6
Silicone-(meth)acrylate-9:
  Molecular weight (formula weight)=422 Silicone-(meth)acrylate-10:
  Molecular weight (formula weight)=408 Silicone-(meth)acrylate-11:
  Molecular weight (Mw)=1,350, Dispersity (Mw/Mn)=1.5
Silicone-(meth)acrylate-12:
  Molecular weight (Mw)=1,400, Dispersity (Mw/Mn)=1.4
Silicone-(meth)acrylate-13:
  Molecular weight (formula weight)=860 Silicone-(meth)acrylate-14:
  Molecular weight (Mw)=1,800, Dispersity (Mw/Mn)=1.5
Silicone-(meth)acrylate-15:
  Molecular weight (Mw)=1,600, Dispersity (Mw/Mn)=1.6
Silicone-(meth)acrylate-16:
  Molecular weight (Mw)=1,600, Dispersity (Mw/Mn)=1.6

The following are Polyurethane-acrylates-1 to 7, Polyimide-acrylate-1, and Polyamide-acrylate-1 each blended to compositions for forming a living body contact layer as a non-silicon-containing resin. Incidentally, the formulae of Polyimide-acrylate-1 and Polyamide-acrylate-1 are average composition formulae.

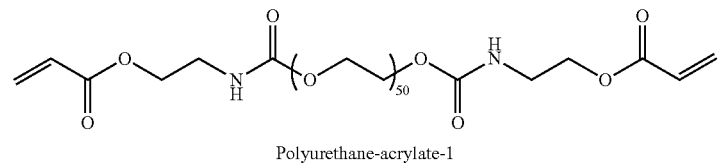

Polyurethane-acrylate-1

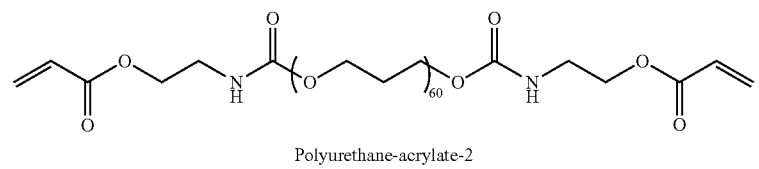

Polyurethane-acrylate-2

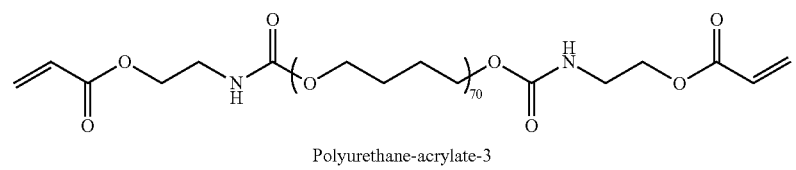

Polyurethane-acrylate-3

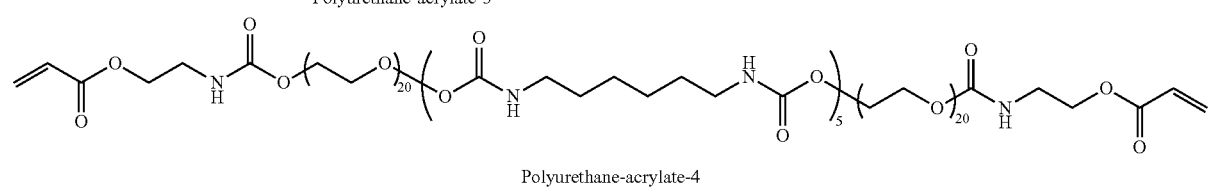

Polyurethane-acrylate-4

-continued

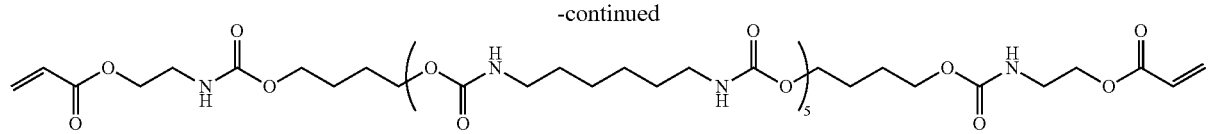
Polyurethane-acrylate-5

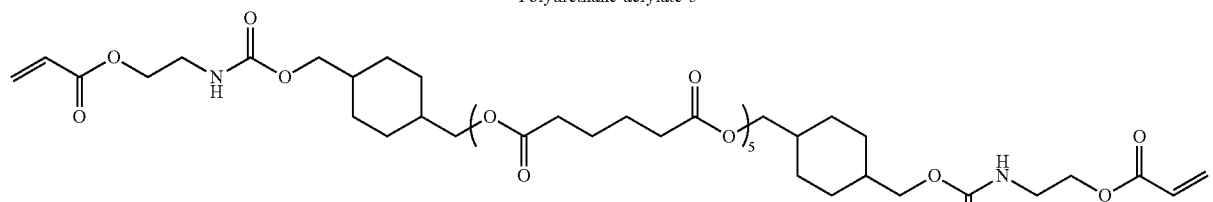
Polyurethane-acrylate-6

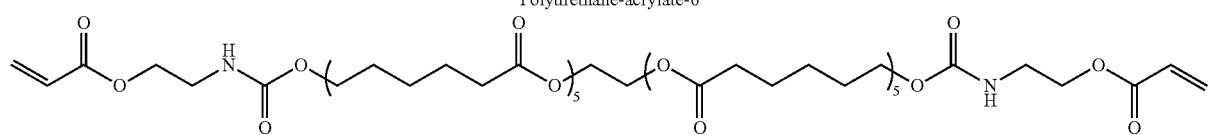
Polyurethane-acrylate-7

(In the formulae, the numbers of repeating units are average values)

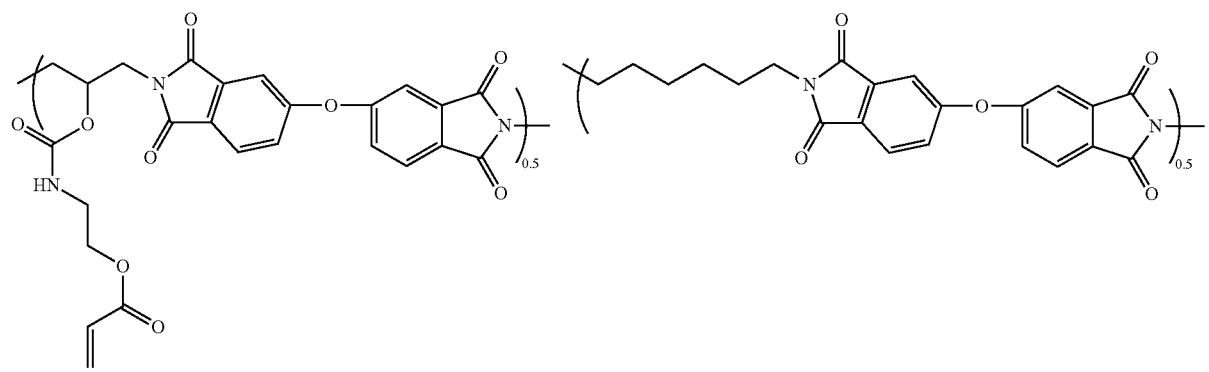
Polyimide-acrylate-1

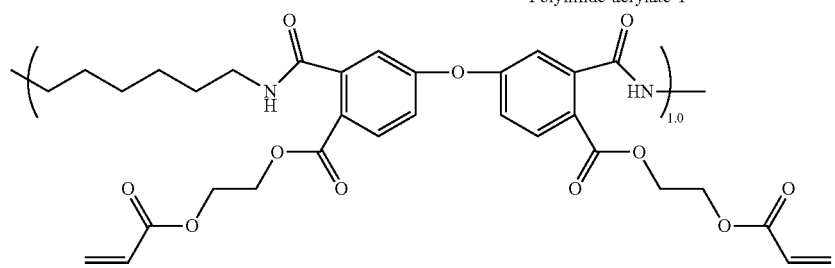
Polyamide-acrylate-1

(In the formulae, the numbers are molar fractions of the repeating units)

Polyurethane-acrylate-1:
 Molecular weight (Mw)=2,600, Dispersity (Mw/Mn)=1.8
Polyurethane-acrylate-2:
 Molecular weight (Mw)=3,800, Dispersity (Mw/Mn)=1.7
Polyurethane-acrylate-3:
 Molecular weight (Mw)=5,400, Dispersity (Mw/Mn)=1.9
Polyurethane-acrylate-4:
 Molecular weight (Mw)=3,100, Dispersity (Mw/Mn)=2.2
Polyurethane-acrylate-5:
 Molecular weight (Mw)=1,450, Dispersity (Mw/Mn)=1.9
Polyurethane-acrylate-6:
 Molecular weight (Mw)=1,980, Dispersity (Mw/Mn)=1.9
Polyurethane-acrylate-7:
 Molecular weight (Mw)=1,480, Dispersity (Mw/Mn)=1.8
Polyimide-acrylate-1:
 Molecular weight (Mw)=2,380, Dispersity (Mw/Mn)=2.6
Polyamide-acrylate-1:
 Molecular weight (Mw)=3,310, Dispersity (Mw/Mn)=2.8

The following are Crosslinking agents-1 to 4 each blended to compositions for forming a living body contact layer as an additive.

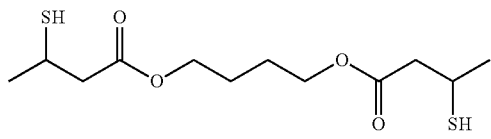

Crosslinking agent-1

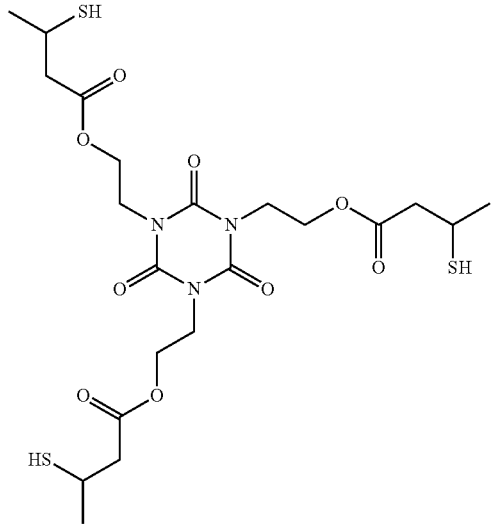

Crosslinking agent-2

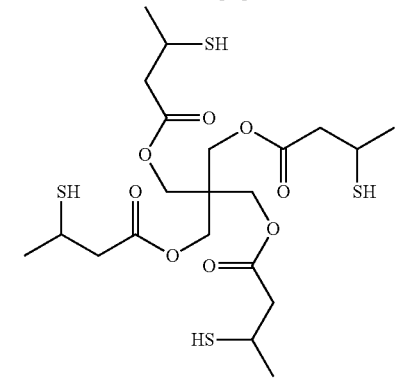

Crosslinking agent-3

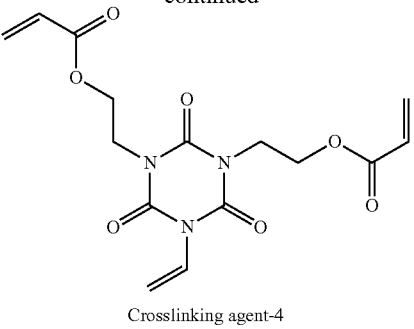

Crosslinking agent-4

The following is Radical generator-1 blended to compositions for forming a living body contact layer as an additive.

Radical generator-1: dimethoxyphenylacetophenone

The following are organic solvents blended to compositions for forming a living body contact layer. PGMEA: propylene glycol-1-monomethyl ether-2-acetate PGME: propylene glycol-1-monomethyl ether Examples 1 to 18, Comparative Examples 1 to 3

The particles, the silicon-containing resin, the non-silicon-containing resin(s), organic solvent(s), and the additives (crosslinking agent and/or radical generator) were blended in each formulation described in Table 1 to prepare solutions of composition for forming a living body contact layer (Sols-1 to 18, Comparative Sols-1 and 2). A copper plate with a thickness of 0.1 mm plated with nickel was placed on a hot plate as an electro-conductive base material. Onto this copper plate, each solution of composition for forming a living body contact layer was dispensed. This was baked at 110° C. for 10 minutes to evaporate the organic solvent. Then, this was pressed by using a quartz substrate on the side of the solution of composition for forming a living body contact layer with a thin release sheet of tetrafluoroethylene being inserted therebetween. Each pressing was carried out under a pressure described in Table 2 (Comparative Example 3 did not perform pressing), while irradiating light with an exposure value of 2 J/cm$^2$ using a halogen lamp, and heating the substrate (each temperature is described in Table 2) in some cases to crosslink and cure the silicon-containing resin and the non-silicon-containing resin to produce each bioelectrode.

TABLE 1

| Composition solution * | Particle (parts by mass) | Silicon-containing resin (parts by mass) | Non-silicon-containing resin (parts by mass) | Organic solvent (parts by mass) | Additives (parts by mass) |
|---|---|---|---|---|---|
| Sol-1 | Au-40 (5) | Silicone-(meth)-acryrate-1 (10) | Polyurethane-acrylate-1 (90) | PGMEA (30) | Crosslinking agent-4 (5) Radical generator-1 (2) |
| Sol-2 | Au-40 (15) | Silicone-(meth)-acryrate-2 (8) | Polyurethane-acrylate-2 (92) | 2-heptanone (50) | Crosslinking agent-1 (10) Radical generator-1 (2) |
| Sol-3 | Ag-30 (15) | Silicone-(meth)-acryrate-3 (8) | Polyurethane-acrylate-3 (92) | 2-heptanone (40) | Crosslinking agent-2 (5) Radical generator-1 (2) |
| Sol-4 | Au-100 (14) | Silicone-(meth)-acryrate-4 (10) | Polyurethane-acrylate-4 (90) | PGMEA (30) | Crosslinking agent-3 (7) Radical generator-1 (2) |
| Sol-5 | Au-40 (5) | Silicone-(meth)-acryrate-5 (8) | Polyurethane-acrylate-5 (92) | PGMEA (30) | Crosslinking agent-1 (5) Crosslinking agent-4 (2) Radical generator-1 (2) |
| Sol-6 | Au-40 (8) | Silicone-(meth)-acryrate-6 (8) | Polyurethane-acrylate-6 (92) | PGMEA (30) | Radical generator-1 (2) |

TABLE 1-continued

| Composition solution * | Particle (parts by mass) | Silicon-containing resin (parts by mass) | Non-silicon-containing resin (parts by mass) | Organic solvent (parts by mass) | Additives (parts by mass) |
|---|---|---|---|---|---|
| Sol-7 | Au-100 (15) | Silicone-(meth)-acryrate-7 (12) | Polyurethane-acrylate-7 (88) | PGMEA (30) | Radical generator-1 (2) |
| Sol-8 | Au-100 (15) | Silicone-(meth)-acryrate-8 (6) | Polyurethane-acrylate-7 (94) | PGME (10) PGMEA (20) | Crosslinking agent-3 (7) Radical generator-1 (2) |
| Sol-9 | Au-100 (10) | Silicone-(meth)-acryrate-9 (3) | Polyurethane-acrylate-7 (97) | PGMEA (30) | Radical generator-1 (2) |
| Sol-10 | Au-100 (10) | Silicone-(meth)-acryrate-10 (3) | Polyurethane-acrylate-7 (97) | PGMEA (20) butyl acetate (10) | Radical generator-1 (2) |
| Sol-11 | Au-100 (10) | Silicone-(meth)-acryrate-11 (8) | Polyurethane-acrylate-7 (92) | Amyl acetate (25) | Radical generator-1 (2) |
| Sol-12 | Au-100 (10) | Silicone-(meth)-acryrate-12 (8) | Polyurethane-acrylate-7 (92) | PGMEA (30) | Radical generator-1 (2) |
| Sol-13 | Au-100 (10) | Silicone-(meth)-acryrate-13 (4) | Polyurethane-acrylate-7 (96) | PGMEA (30) | Radical generator-1 (2) |
| Sol-14 | Au-100 (10) | Silicone-(meth)-acryrate-14 (15) | Polyurethane-acrylate-7 (85) | PGMEA (30) | Radical generator-1 (2) |
| Sol-15 | Au-100 (10) | Silicone-(meth)-acryrate-15 (5) | Polyurethane-acrylate-7 (95) | PGMEA (30) | Radical generator-1 (2) |
| Sol-16 | Au-100 (10) | Silicone-(meth)-acryrate-16 (8) | Polyurethane-acrylate-7 (92) | PGMEA (30) | Radical generator-1 (2) |
| Sol-17 | Au-100 (10) | Silicone-(meth)-acryrate-16 (8) | Polyurethane-acrylate-1 (62) Polyimide-acrylate-1 (30) | PGMEA (30) | Radical generator-1 (2) |
| Sol-18 | Au-100 (10) | Silicone-(meth)-acryrate-16 (8) | Polyurethane-acrylate-1 (92) Polyamide-acrylate-1 (30) | PGMEA (30) | Radical generator-1 (2) |
| Comparative Sol-1 | Au-100 (10) | — | Polyurethane-acrylate-1 (100) | PGMEA (30) | Radical generator-1 (2) |
| Comparative Sol-2 | Au-100 (10) | Silicone-(meth)-acryrate-1 (100) | — | PGMEA (30) | Radical generator-1 (2) |

* solution of composition for forming a living body contact layer

It is to be noted that each of the bio-electrodes produced in Examples 1 to 18 was the bio-electrode 1 having the living body contact layer 3 composed of the particles 4 and the resin layer 5 formed on the electro-conductive base material 2, with the particles 4 being exposed convexly from the surface of the resin layer 5, as shown in FIG. 1. The resin layer 5 contained both of the silicon-containing resin and the non-silicon-containing resin, with the silicon-containing resin being localized in the direction of the surface of the resin layer.

Figure 4:
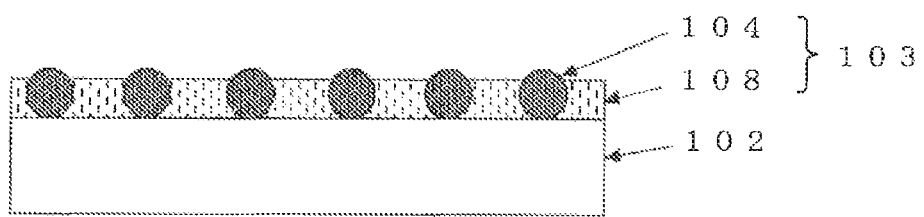
FIG. 4 is a schematic sectional view showing the bio-electrode of Comparative Example 1, in which the resin layer was formed from a non-silicon-containing resin alone.
Figure 5:
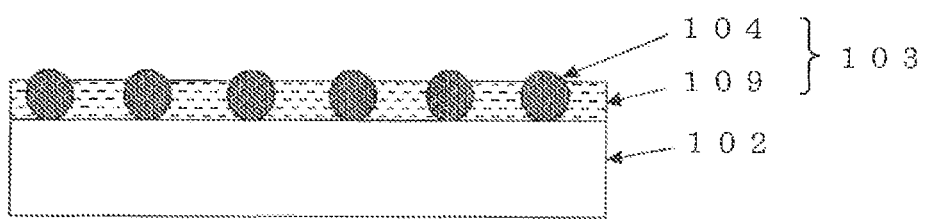
FIG. 5 is a schematic sectional view showing the bio-electrode of Comparative Example 2, in which the resin layer was formed from a silicon-containing resin alone.

On the other hand, the bio-electrode produced in Comparative Example 1 was the bio-electrode 101 shown in FIG. 4, in which the living body contact layer 103 composed of the particles 104 and the non-silicon-containing resin layer 108 was formed on the electro-conductive base material 102, and the particles 104 were exposed convexly from the surface of the non-silicon-containing resin layer 108. The bio-electrode produced in Comparative Example 2 was the bio-electrode 111 shown in FIG. 5, in which the living body contact layer 103 composed of the particles 104 and the silicon-containing resin layer 109 was formed on the electro-conductive base material 102, and the particles 104 were exposed convexly from the surface of the silicon-containing resin layer 109. The bio-electrode produced in Comparative Example 3 was the bio-electrode 121 shown in FIG. 6, in which the living body contact layer 103 composed of the particles 104 and the resin layer 105 was formed on the electro-conductive base material 102, and the particles 104 were not exposed from the surface of the resin layer 105. The resin layer 105 contained both of the silicon-containing resin and the non-silicon-containing resin, with the silicon-containing resin being localized in the direction of the surface of the resin layer.

(Evaluation of Repellency)

On each of the produced bio-electrodes, contact angle of the resin layer with water was measured. The results are shown in Table 2.

(Measuring Thickness of Resin Layer)

The produced bio-electrode was sliced with a cutter. The cross section was observed under an electron microscope to measure the thickness of the resin layer. The results are shown in Table 2.

(Evaluation of Electric Conductivity)

The electric conductivity of the produced bio-electrode was evaluated by measuring the resistivity using a method in conformity to JIS K 6271 with a Voltage/Current Generator 6241A manufactured by ADC CORPORATION. The results are shown in Table 2.

(Evaluation of Adhesion Properties)

The produced bio-electrode was bended to the angle of 90° for 10 times to observe whether the particles were separated from the bio-electrode or not. The results are shown in Table 2.

TABLE 2

| | Composition solution* | Pressure (kg/cm²) | Temperature (° C.) | Average particle size of particles (μm) | Resin layer thickness (μm) | Electric resistance (Ω) | Contact angle with water (°) | Separation of particles after bending |
|---|---|---|---|---|---|---|---|---|
| Example 1 | Sol-1 | 2 | 23 | 40 | 36 | 28 | 68 | None |
| Example 2 | Sol-2 | 2 | 23 | 40 | 36 | 26 | 69 | None |
| Example 3 | Sol-3 | 0.5 | 30 | 30 | 29 | 23 | 66 | None |
| Example 4 | Sol-4 | 2 | 40 | 100 | 95 | 13 | 65 | None |
| Example 5 | Sol-5 | 3 | 50 | 40 | 38 | 30 | 67 | None |
| Example 6 | Sol-6 | 0.2 | 30 | 40 | 40 | 40 | 70 | None |
| Example 7 | Sol-7 | 5 | 23 | 100 | 91 | 16 | 71 | None |
| Example 8 | Sol-8 | 3 | 23 | 100 | 93 | 17 | 69 | None |
| Example 9 | Sol-9 | 1.3 | 23 | 100 | 97 | 21 | 63 | None |
| Example 10 | Sol-10 | 1.3 | 23 | 100 | 97 | 22 | 63 | None |
| Example 11 | Sol-11 | 1.4 | 23 | 100 | 96 | 19 | 66 | None |
| Example 12 | Sol-12 | 0.5 | 23 | 100 | 98 | 17 | 65 | None |
| Example 13 | Sol-13 | 2 | 23 | 100 | 93 | 38 | 66 | None |
| Example 14 | Sol-14 | 2 | 25 | 100 | 94 | 31 | 61 | None |
| Example 15 | Sol-15 | 2 | 25 | 100 | 92 | 28 | 66 | None |
| Example 16 | Sol-16 | 2 | 25 | 100 | 93 | 22 | 65 | None |
| Example 17 | Sol-17 | 2 | 25 | 100 | 93 | 28 | 64 | None |
| Example 18 | Sol-18 | 2 | 23 | 100 | 93 | 29 | 69 | None |
| Comparative Example 1 | Comparative Sol-1 | 2 | 23 | 100 | 97 | 15 | 48 | None |
| Comparative Example 2 | Comparative Sol-2 | 2 | 23 | 100 | 91 | 18 | 73 | Separated |
| Comparative Example 3 | Sol-1 | 0 | 23 | 40 | 76 | $10^3$ | 68 | None |

*solution of composition for forming a living body contact layer

As shown in Table 2, in each Examples 1 to 18, which cured the resin with pressing to make the thickness of the resin layer be thinner than the average particle size of the particles, good electric conductivity was obtained without loading large amount of particles; and a lighter bio-electrode could be produced at lower cost since the particles was loaded in a smaller amount. Examples 1 to 18 also revealed that each contact angle with water was large, which indicated high repellency. The bio-electrode was bended without causing separation of the particles, which revealed high adhesion properties between the resin layer and the particles.

On the other hand, in Comparative Example 1, which formed the resin layer from a non-silicon-containing resin (polyurethane-acrylate) only, the repellency was inferior to that of Examples 1 to 18. In Comparative Example 2, which formed the resin layer from a silicon-containing resin (silicone-(meth)acrylate) only, the repellency was high, but the particles had separated after bending, which indicated low adhesion properties between the resin layer and the particles. In Comparative Example 3, which cured the resin without pressing to make the resin layer have a thickness thicker than the average particle size of the particles, the resistivity was large and the electric conductivity was extremely low since the particles were not exposed from the surface of the resin layer.

From the above, it was revealed that the inventive bio-electrode is superior in electric conductivity and biocompatibility, light in weight, can be manufactured at low cost, and can combine repellency of the resin layer surface and adhesion properties of the resin layer to particles.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A bio-electrode comprising an electro-conductive base material and a living body contact layer formed on the electro-conductive base material; wherein the living body contact layer comprises a resin layer and particles dispersed in the resin layer, the particles being coated with gold, platinum, silver, or alloy of these metals; a thickness of the resin layer is equal to or thinner than an average particle size of the particles; the resin layer contains a silicon-containing resin and a non-silicon-containing resin; the silicon-containing resin is localized in a direction of a surface of the resin layer; the silicon-containing resin contains one or more moieties selected from an ester bond, an amide bond, an imide bond, a urethane bond, a thiourethane bond, and a urea bond, together with a (meth)acrylate group; and the non-silicon-containing resin contains one or more moieties selected from an ester bond, an amide bond, an imide bond, a urethane bond, a thiourethane bond, and a thiol group, together with a (meth)acrylate group.

2. The bio-electrode according to claim 1, wherein the average particle size of the particles is 1 μm or more and 1,000 μm or less, and the thickness of the resin layer is 0.5 μm or more and 1,000 μm or less.

3. The bio-electrode according to claim 1, wherein a ratio of the thickness of the resin layer to the average particle size of the particles is 0.5 or more and 1.0 or less.

4. The bio-electrode according to claim 1, wherein the particles constitute 0.5% or more and 50% or less in a volume ratio on the basis of a total volume of the resin layer and the particles.

5. The bio-electrode according to claim 1, wherein the resin layer is a cured product of a resin composition comprising the silicon-containing resin and the non-silicon-containing resin, and each of the silicon-containing resin and the non-silicon-containing resin is at least one of a thermosetting resin and a photo-curable resin.

6. The bio-electrode according to claim 1, wherein the electro-conductive base material comprises one or more species selected from gold, silver, silver chloride, platinum, aluminum, magnesium, tin, tungsten, iron, copper, nickel, stainless, chromium, titanium, and carbon.

7. The bio-electrode according to claim 1, wherein the particles are spherical particles.

8. The bio-electrode according to claim 1, wherein the particles are resin particles or inorganic particles coated with gold, platinum, silver, or an alloy of these metals; the resin particles comprising one or more resins selected from polyacrylate, polyethylene, polypropylene, polystyrene, silicone, and polyurethane; and the inorganic particles comprising any one of glass, silica, and quartz.

9. The bio-electrode according to claim 1, wherein the particles each have an electro-conductive metal layer comprising one or more electro-conductive metals selected from silver, aluminum, copper, nickel, tungsten, and tin in an interior of the particle.

10. The bio-electrode according to claim 1, wherein the thickness of the resin layer is thinner than the average particle size of the particles, and the particles are exposed convexly from the surface of the resin layer.

11. The bio-electrode according to claim 1, wherein the particles are disposed such that each of the particles is the only particle in a respective thickness direction of the resin layer.

* * * * *